(12) United States Patent
Lerner et al.

(10) Patent No.: US 11,593,243 B2
(45) Date of Patent: Feb. 28, 2023

(54) DYNAMIC EMOTION DETECTION BASED ON USER INPUTS

(71) Applicant: Imperva, Inc., San Mateo, CA (US)

(72) Inventors: Aiah Lerner, Tel-Aviv (IL); Jonathan R. Azaria, Beit Gamliel (IL); Matan Lion, Tel-Aviv (IL)

(73) Assignee: Imperva, Inc., San Mateo, CA (US)

( * ) Notice: Subject to any disclaimer, the term of this patent is extended or adjusted under 35 U.S.C. 154(b) by 35 days.

(21) Appl. No.: 17/137,333

(22) Filed: Dec. 29, 2020

(65) Prior Publication Data

US 2022/0206918 A1   Jun. 30, 2022

(51) Int. Cl.
| | |
|---|---|
| *G06F 3/00* | (2006.01) |
| *G06F 11/30* | (2006.01) |
| *G06F 11/34* | (2006.01) |
| *G06F 3/023* | (2006.01) |
| *G06F 3/0354* | (2013.01) |
| *A61B 5/16* | (2006.01) |

(52) U.S. Cl.
CPC .......... *G06F 11/3041* (2013.01); *A61B 5/165* (2013.01); *G06F 3/023* (2013.01); *G06F 3/03543* (2013.01); *G06F 11/3438* (2013.01)

(58) Field of Classification Search
None
See application file for complete search history.

(56) References Cited

U.S. PATENT DOCUMENTS

| | | | |
|---|---|---|---|
| 8,396,719 B2 | 3/2013 | Patrick et al. | |
| 8,683,348 B1 * | 3/2014 | Blank | G06F 3/038 715/709 |
| 9,953,231 B1 * | 4/2018 | Medina, III | G06F 21/32 |
| 2010/0030714 A1 * | 2/2010 | Bollano | G10L 17/26 706/54 |
| 2014/0317744 A1 | 10/2014 | Turgeman et al. | |
| 2016/0364002 A1 * | 12/2016 | Gates | G06F 3/017 |
| 2018/0307661 A1 * | 10/2018 | McDuff | G06F 16/9535 |
| 2018/0350455 A1 * | 12/2018 | Rosen | G06F 16/951 |
| 2019/0332752 A1 * | 10/2019 | Gordon | G06F 21/552 |

OTHER PUBLICATIONS

Kaveh Bakhtiyari et al., "Implementation of Emotional-Aware Computer Systems Using Typical Input Devices," 2014, pp. 364-374, Springer International Publishing, Switzerland.
Rayhan Shikder et al., "Keystroke/Mouse Usage Based Emotion Detection and User Identification," Jan. 2017, 10 pages, IEEE.

* cited by examiner

*Primary Examiner* — Henry Tsai
*Assistant Examiner* — Dean Phan
(74) *Attorney, Agent, or Firm* — Nicholson, De Vos, Webster & Elliott, LLP

(57) ABSTRACT

A method by a network device for dynamically detecting emotional states of a user operating a client end station to interact with an application. The method includes receiving information regarding user inputs received by the client end station from the user while the user interacted with the application during a particular time period and determining an emotional state of the user based on analyzing the information and information regarding user inputs received by the client end station from the user while the user interacted with the application during one or more previous time periods that together with the particular time period form a time window.

20 Claims, 5 Drawing Sheets

DYNAMIC EMOTION DETECTION BASED ON USER INPUTS

TECHNICAL FIELD

Embodiments of the invention relate to the field of emotion detection, and more specifically, to dynamically detecting emotional states of users based on user inputs.

BACKGROUND

A graphical user interface is a form of user interface that allows users to interact with an application through the manipulation of graphical elements on a display screen. A user may use one or more input devices when interacting with an application via a graphical user interface such as a keyboard, mouse, and/or touchscreen. The design of the graphical user interface is an important part of application/software development with the goal typically being to make the graphical user interface aesthetically pleasing and easy to use for the users. A graphical user interface that is difficult to use may cause users to get frustrated and even angry.

The application developer may want to receive feedback regarding the experience users are having when interacting with the application via the graphical user interface. One way for the application developer to receive feedback is to send surveys to the users. However, surveys are intrusive and can hamper the user experience. Also, there are many biases to account for when dealing with surveys. For example, users may tend to lie when answering surveys to feel better about themselves, exaggerate events that happened more recently, and/or downplay events that happened less recently.

Another way for the application developer to receive feedback regarding the user experience is to use analytics tools. For example, a website analytics tool can be used to track website activity such as session duration, pages per session, and/or bounce rate of users visiting the website. Analytics tools can be used to better channel traffic and to provide targeted/tailored advertisements to users. However, they do not help with understanding the user's frustrations. For example, users may find the website very uninformative and difficult to use, but this may not necessarily be reflected in the website analytics.

BRIEF DESCRIPTION OF THE DRAWINGS

The invention may best be understood by referring to the following description and accompanying drawings that are used to illustrate embodiments of the invention. In the drawings.

DETAILED DESCRIPTION

Figure 1:
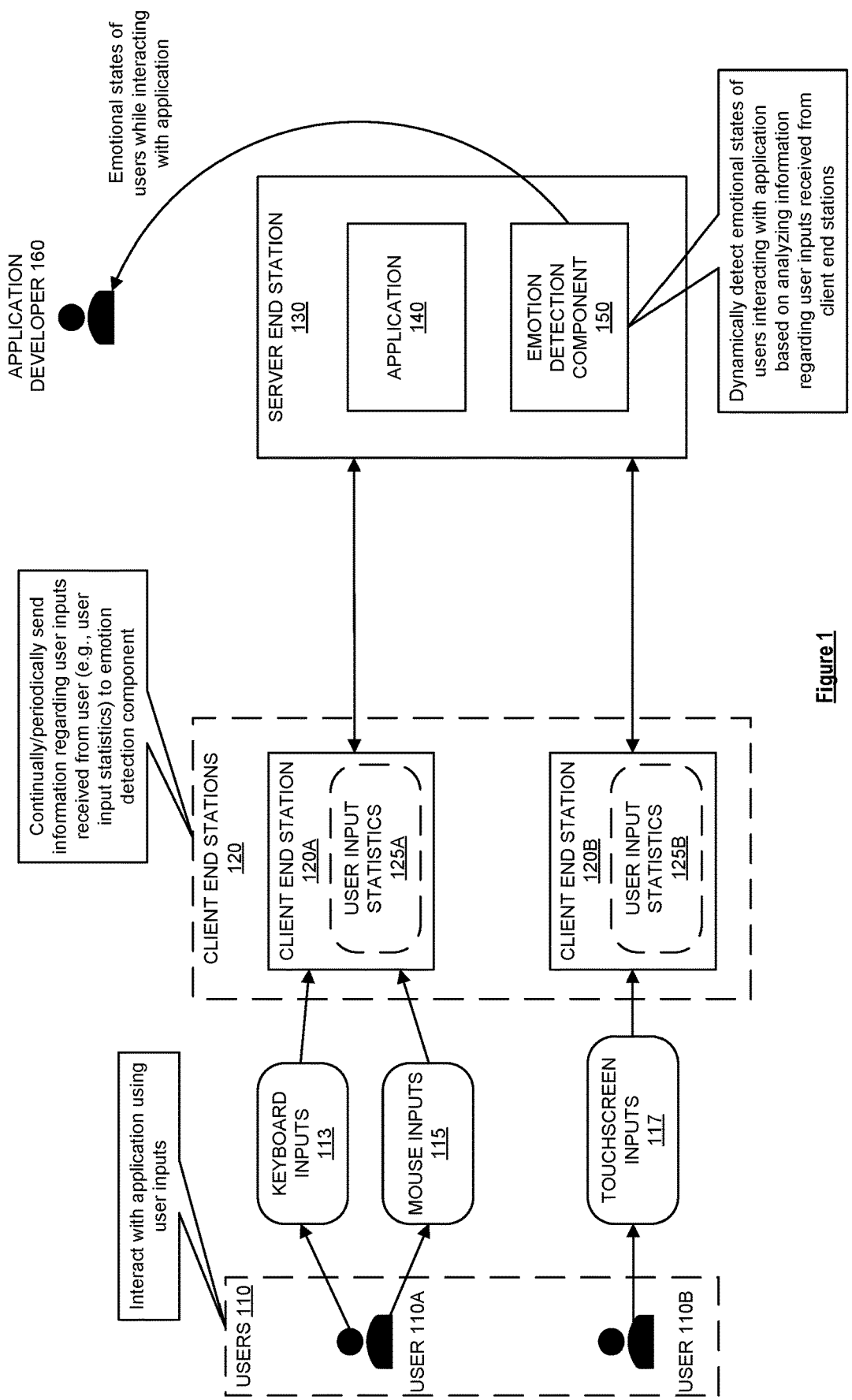
FIG. 1 is a block diagram of a system in which dynamic emotion detection can be implemented, according to some embodiments.

In the following description, numerous specific details such as logic implementations, resource partitioning/sharing/duplication implementations, types and interrelationships of system components, and logic partitioning/integration choices are set forth in order to provide a more thorough understanding of the present invention. It will be appreciated, however, by one skilled in the art that the invention may be practiced without such specific details. In other instances, control structures, gate level circuits and full software instruction sequences have not been shown in detail in order not to obscure the invention. Those of ordinary skill in the art, with the included descriptions, will be able to implement appropriate functionality without undue experimentation.

Bracketed text and blocks with dashed borders (e.g., large dashes, small dashes, dot-dash, and dots) are used herein to illustrate optional operations that add additional features to embodiments of the invention. However, such notation should not be taken to mean that these are the only options or optional operations, and/or that blocks with solid borders are not optional in certain embodiments of the invention.

References in the specification to "one embodiment," "an embodiment," "an example embodiment," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

In the following description and claims, the terms "coupled" and "connected," along with their derivatives, may be used. It should be understood that these terms are not intended as synonyms for each other. "Coupled" is used to indicate that two or more elements, which may or may not be in direct physical or electrical contact with each other, co-operate or interact with each other. "Connected" is used to indicate the establishment of communication between two or more elements that are coupled with each other As used herein, a network device (e.g., a router, switch, bridge) is an electronic device that is a piece of networking equipment, including hardware and software, which communicatively interconnects other equipment on the network (e.g., other network devices, end stations). Some network devices are "multiple services network devices" that provide support for multiple networking functions (e.g., routing, bridging, and/or switching), and/or provide support for multiple application services (e.g., data, voice, and video).

As used herein, server end stations are network devices operable to execute or otherwise implement one or more servers providing content or services to clients. For example, server end stations may implement web application servers, database servers, file servers, print servers, mail servers, gaming servers, application servers, and/or Domain Name System (DNS) servers.

As used herein, client end stations (e.g., workstations, laptops, netbooks, palm tops, mobile phones, smartphones, multimedia phones, Voice over Internet Protocol (VoIP) phones, user equipment (UE), terminals, portable media players, Global Positioning Satellite (GPS) units, gaming systems, set-top boxes) are network devices operable to execute or otherwise implement applications that, among other functions, can access the content and/or services provided by servers over a network (e.g., over a local area network (LAN), over the Internet, and/or over virtual private networks (VPNs) overlaid on (e.g., tunneled through) the Internet).

As mentioned above, an application developer may want to receive feedback regarding the experience users are having when interacting with an application via a graphical user interface. The application developer may use surveys or analytics tools to receive such feedback. However, surveys are intrusive, hamper the user experience, and may suffer from bias, and analytics tools may not necessarily capture the user's frustrations.

Embodiments disclosed herein overcome one or more drawbacks of existing techniques by dynamically determining the emotional states of users interacting with an application based on analyzing information regarding user inputs provided by the users while the users interacted with the application. Embodiments may be less intrusive compared to surveys and may not suffer from user bias. Also, embodiments may help an application developer understand which aspects of their application are causing frustration for users, which may help the application developer improve the user experience.

An embodiment is a method by a network device for dynamically detecting emotional states of a user operating a client end station to interact with an application hosted by a server end station. The method includes receiving first information regarding user inputs received by the client end station from the user while the user interacted with the application during a first time period, determining a first emotional state of the user based on analyzing the first information and information regarding user inputs received by the client end station from the user while the user interacted with the application during one or more time periods previous to the first time period that together with the first time period form a first time window, receiving second information regarding user inputs received by the client end station from the user while the user interacted with the application during a second time period, and determining a second emotional state of the user based on analyzing the second information and information regarding user inputs received by the client end station from the user while the user interacted with the application during one or more time periods previous to the second time period including at least the first time period that together with the second time period form a second time window. Embodiments are further described herein with reference to the accompanying figures.

FIG. 1 is a block diagram of a system in which dynamic emotion detection can be implemented, according to some embodiments. As shown in the diagram, the system includes client end stations 120 (e.g., client end stations 120A and 120B) that are communicatively coupled to a server end station 130 (e.g., over a network such as the internet). Users 110 may operate client end stations 120 to interact with an application 140 implemented by the server end station 130. In one embodiment, the application 140 is a web application. In such an embodiment, the client end stations 120 may access the web application, for example, by generating one or more web application layer requests (e.g., Hypertext Transfer Protocol (HTTP) request messages such as a "POST" HTTP request messages or "GET" HTTP request messages) and sending these web application layer requests to the server end station 130. In response to receiving web application layer requests, the server end station 130 may send corresponding web application layer responses (e.g., HTTP response messages) containing the data/content of the web application to the client end stations 120. The client end stations 120 may then render the contents of the web application layer responses (e.g., on a display screen for a user) or otherwise consume the contents of the web application layer responses.

The users 110 may use one or more user input methods to interact with the application 140 (e.g., via a graphical user interface (GUI)). For example, as shown in the diagram, user 110A may provide keyboard inputs 113 and mouse inputs 115 to client end station 120A (e.g., if client end station 120A is a laptop/desktop computer) to interact with the application 140 and user 110B may provide touchscreen inputs 117 to client end station 120B (e.g., if client end station 120B is a smartphone or tablet) to interact with the application 140. The user input methods shown in the diagram are provided by way of example. It should be understood that the users 110 may interact with the application 140 using other types of input methods. For example, the users 110 may interact with the application 140 using microphone inputs (e.g., providing audio data), camera inputs (e.g., providing image/video data), accelerometer inputs (e.g., providing tilt/movement data), and/or biometric inputs (e.g., providing heartbeat data) to the client end stations 120 to interact with the application 140.

As shown in the diagram, the server end station 130 implements an emotion detection component 150. As will be described further herein, the emotion detection component 150 may dynamically determine the emotional states of the users 110 (e.g., whether a user is happy, sad, angry, frustrated, amused, surprised, fear, and/or disgusted) interacting with the application 140 based on analyzing information regarding the user inputs received by the client end stations 120 from the users 110 while the users 110 interacted with the application 140. While the diagram shows the application 140 and the emotion detection component 150 being implemented by the same server end station 130, in other embodiments the application 140 and the emotion detection component 150 may be implemented by different server end stations 130.

The client end stations 120 may send information regarding the user inputs they received from the users 110 while the users 110 interacted with the application 140 (such information may be referred to herein as "user input information") to the emotion detection component 150. The client end stations 120 may continually/periodically send user input information to the emotion detection component 150 as they receive additional user inputs, where each user input information that is sent covers user inputs received during a particular time period. For example, every N seconds, client end station 120A may generate and send information regarding the keyboard inputs 113 and mouse inputs 115 it received from user 110A while user 110A interacted with the application 140 during the previous N seconds to the emotion detection component 150. Similarly, every N seconds, client end station 120B may generate information regarding the touchscreen inputs 117 it received from user 110B while user 110B interacted with the application 140 during the previous N seconds to the emotion detection component 150. In this example, the time periods have fixed lengths (N seconds). However, in other embodiments, the time periods may have variable lengths. For example, a client end station 120 may generate and send user input information to the emotion detection component 150 whenever it has received a threshold amount of user inputs since the last time the client end station 120 sent user input information to the emotion detection component 150, whenever the user 110 performs certain actions (e.g., whenever the user clicks/presses a link to move to another page/screen of the application 140), or responsive to another type of event (e.g., whenever the emotion detection component 150 makes a request to the client end station 120 to send user input information). In an embodiment where the application 140 is a web application, the server end station 130 (e.g., the application 140 or the emotion detection component 150) may send JavaScript code to the client end stations 120 that when executed by the client end stations 120 causes the client end stations 120 to generate and send user input information to the emotion detection component 150 in the manner described herein.

In one embodiment, the user input information that a client end station 120 sends to the emotion detection component 150 includes statistical information regarding the user inputs received by the client end station 120 from a user 110 while the user 110 interacted with the application 140 during a particular time period. For example, the user input information that client end station 120A sends to the emotion detection component 150 may include statistical information (e.g., average, maximum, and/or minimum) generated by client end station 120A (e.g., user input statistics 125A) describing the keyboard inputs 113 and mouse inputs 115 that client end station 120A received from user 110A during a time period. Statistical information regarding keyboard inputs may include statistical information regarding key down to key up time length, statistical information regarding key up to key down time length, and/or statistical information regarding a number of keys pressed. Statistical information regarding mouse inputs may include statistical information regarding x-axis movement speed, statistical information regarding y-axis movement speed, statistical information regarding a number of clicks, statistical information regarding click to unclick time length, statistical information regarding unclick to click time length, statistical information regarding x-axis direction changes, statistical information regarding y-axis direction changes, and/or statistical information regarding time lengths between close clicks.

Similarly, the user input information that client end station 120B sends to the emotion detection component 150 may include statistical information (e.g., average, maximum, and/or minimum) generated by client end station 120B (e.g., user input statistics 125B) describing the touchscreen inputs 117 that client end station 120B received from user 110B during a particular time period. Statistical information regarding touchscreen inputs may include statistical information regarding x-axis swipe speed, statistical information regarding y-axis swipe speed, statistical information regarding a number of touches, statistical information regarding finger down to finger up time length, statistical information regarding finger up to finger down time length, statistical information regarding touch intensity, statistical information regarding x-axis direction changes, and statistical information regarding y-axis direction changes, and/or statistical information regarding time lengths between close taps.

A benefit of sending statistical information to the emotion detection component 150 (as opposed to sending raw/unprocessed information) is that it reduces the amount of data that is sent to the emotion detection component 150 thereby saving bandwidth and that it distributes some of the data processing tasks to the client end stations 120, which helps reduce the amount of processing that needs to be performed at the emotion detection component 150, which allows the system to scale better. Another benefit of the client end stations 120 sending statistical information to the emotion detection component 150 is that it may help preserve the anonymity of the users 110 (e.g., by not sending raw/unprocessed sensitive data).

Thus, the emotion detection component 150 may continually/periodically receive, from each of the client end stations 120, information regarding user inputs received by that client end station 120 from a user 110 while the user 110 interacted with the application 140 during a particular time period. The emotion detection component 150 may dynamically determine the emotional states of each of the users 110 as it receives user input information from the client end stations 120. The emotion detection component 150 may dynamically determine the emotional state of the users 110 based on analyzing the user input information using a sliding window, where each time window includes multiple time periods. For example, if the emotion detection component 150 receives user input information from client end station 120A covering a particular time period, it may determine the emotional state of user 110A based on analyzing the user input information covering that particular time period as well as user input information covering one or more previous time periods that together with the particular time period form a time window. Similarly, if the emotion detection component 150 receives user input information from client end station 120B covering a particular time period, it may determine the emotional state of user 110B based on analyzing the user input information covering that particular time period as well as user input information covering one or more previous time periods that together with the particular time period form a time window. The size of the sliding window may be configurable depending on the implementation (e.g., each time window may include three time periods). In one embodiment, the emotion detection component 150 determines the emotional state of a user at a particular time based on the immediately previously determined emotional state of the user (e.g., if the user was most recently in a happy emotional state then the user is more likely to currently still be in a happy emotional state and less likely to currently be in a angry/sad emotional state). The emotion detection component 150 may use such a sliding window approach to dynamically determine the emotional states of the users 110 as it receives new user input information from the client end stations 120 over time.

The emotion detection component 150 may use a machine learning system to determine the emotional states of the users 110. The machine learning system may be trained to determine the emotional states of users based on the user inputs provided by the users. The machine learning system may be trained using KNN (K-nearest neighbors), KStar, Random Committee, Random Forest, or similar machine learning algorithm/classifier. In one embodiment, the emotion detection component 150 receives user input information that is tagged with the emotional states of users (e.g., which may have been provided by users willing to participate in providing their emotional states (e.g., via a survey) to help with training the machine learning system) and uses this information to train the machine learning system.

The determined emotional states of the users 110 may be used in different ways depending on the implementation. In one embodiment, as shown in the diagram, the emotion detection component 150 sends information regarding the determined emotional states of the users 110 to an application developer 160 as feedback (to help the application developer 160 understand how the users 110 are experiencing the application 140). In one embodiment, the emotion detection component 150 determines a user interface element of the application that a user interacted with when the user was determined to be in a particular emotional state (e.g., based on user input information such as the location of the mouse cursor or which textbox/buttons were activated) and sends an indication to the application developer 160 that the user interface element is associated with the particular emotional state. The application developer 160 may use such information to determine which specific aspects of the application's user interface are causing users to respond emotionally (e.g., either negatively or positively). The application developer 160 may use the feedback to improve the user experience.

In one embodiment, dynamic emotion detection techniques are used during A/B testing to better determine which user interfaces are more preferred by users. A/B testing is process of showing two variants of a user interface to different segments of users and comparing which variant elicits a more favorable response. For example, the application 140 may provide two different user interfaces (e.g., that have similar functionality) to different users 110. The emotion detection component 150 may then determine the emotional states of each of the users 110 while the users 110 interacted with the application via the respective user interfaces. The emotion detection component 150 may then send an indication to the application developer 160 of the emotional states of the different users while those users interacted with the different user interfaces. This may help the application developer 160 understand which variant of the user interface elicits more positive emotions from the users 110.

In one embodiment, the emotion detection component 150 determines emotional patterns of the users 110 (e.g., how the emotional states of the users 110 changed over time). The emotional patterns of the users may be used to determine whether the users are a bot user (e.g., automated software) or not. For example, the emotional pattern of a user, along with other attributes associated with the user (e.g., Internet Protocol (IP) address, web browser type, etc.), may be used to generate a fingerprint of the user. Fingerprints are commonly used in bot detection to help distinguish between different users/devices. Using the emotional pattern of the user may help better distinguish different users/devices (e.g., an intense user may have an emotional pattern that goes from frustration to anger to happiness, a more relaxed user may have an emotional pattern that casually shifts between a small number of emotional states, and a bot user may have a single emotional state), which may help detect bots at a finer level of granularity.

As another example, the emotional pattern of a user may be matched against known emotional patterns, where each of the known emotional patterns is associated with a security risk level. For example, the known emotional patterns may include an emotional pattern that has been found to be typically associated with a human user and an emotional pattern that has been found to be typically associated with a bot user (e.g., automated software), where the emotional pattern that has been found to be typically associated with a human user may be associated with a relatively lower security risk level while the emotional pattern that has been found to be typically associated with a bot user (e.g., one that shows little to no emotion) may be associated with a relatively higher risk level. If the emotional pattern of the user matches one of the known emotional patterns, then the user may be assigned the security risk level associated with the matching emotional pattern. In one embodiment, if the emotional pattern of the user does not match any of the known emotional patterns, then the user is assigned the highest risk level. The security risk level assigned to the user can be taken into consideration when determining whether the user is a bot user or a human user.

While a certain arrangement of components is shown in the diagram, it should be understood that other arrangements are also possible. For example, as mentioned above, the application 140 and the emotion detection component 150 may be implemented by different server end stations. In one embodiment, the application 140 and/or the emotion detection component 150 are implemented in the "cloud."

Figure 2:
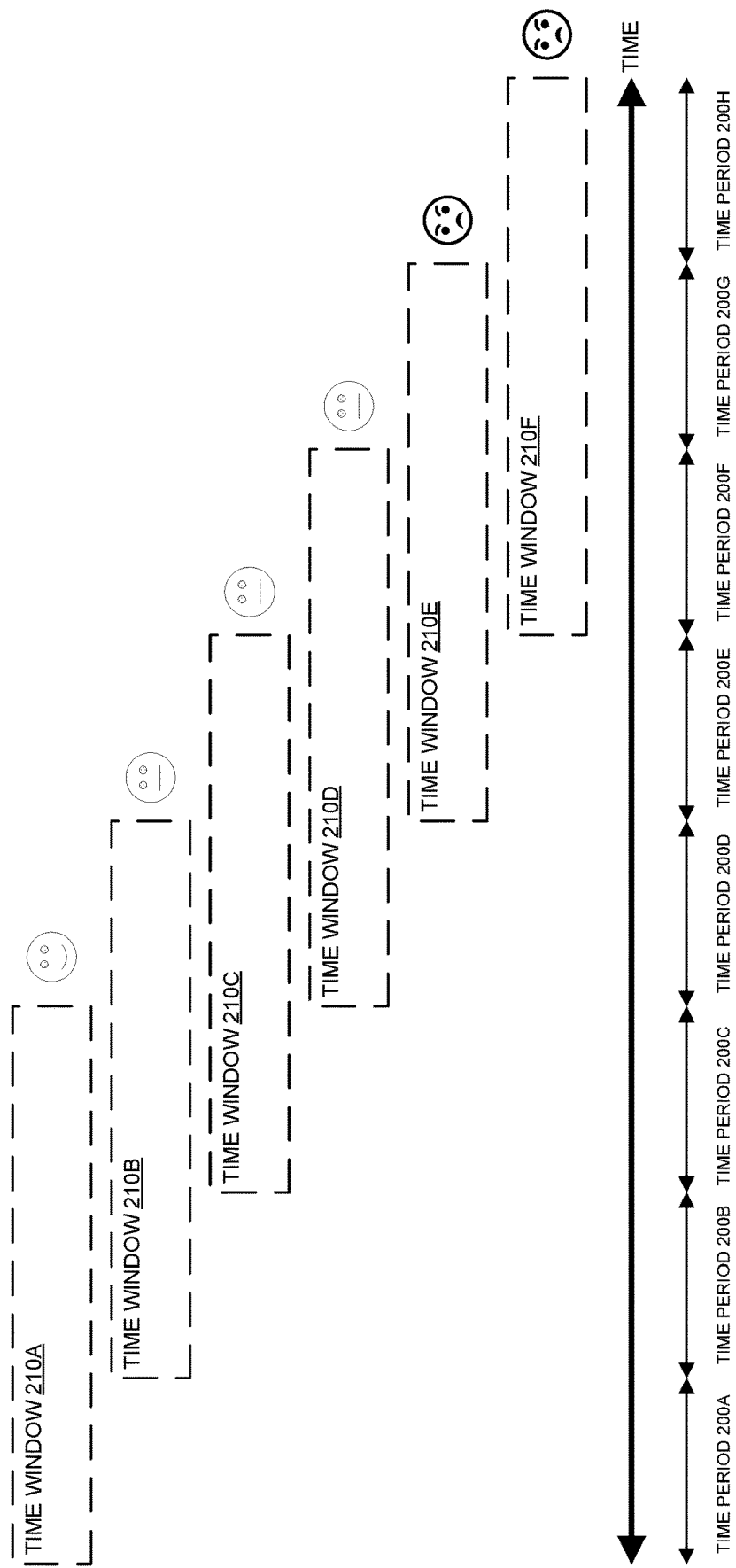
FIG. 2 is a diagram illustrating dynamic emotion detection using a sliding window, according to some embodiments.

FIG. 2 is a diagram illustrating dynamic emotion detection using a sliding window, according to some embodiments. As mentioned above, a client end station 120 may continually/periodically send user input information to the emotion detection component 150 in time period increments/chunks. For example, the client end station 120 may send user input information covering time period 200A to the emotion detection component 150 after time period 200A, send user input information covering time period 200B after time period 200B, and so on for time periods 200C-H.

As mentioned above, the emotion detection component 150 may dynamically determine the emotional states of a user based on analyzing user input information using a sliding window. Each time window may include multiple consecutive time periods. In the example shown in the diagram, each time window 210 includes three time periods 200. For example, as shown in the diagram, time window 210A includes time periods 200A-C, time window 210B includes time periods 200B-D, time window 210C includes time periods 200C-E, time window 210D includes time periods 200D-F, time window 210E includes time periods 200E-G, and time window 210F includes time periods 200E-H.

After receiving user input information covering time window 210A (i.e., user input information covering time periods 200A-C), the emotion detection component 150 may determine the emotional state of the user after time window 210A based on analyzing that user input information. In this example, the emotion detection component 150 determines that the user is in a happy emotional state after time window 210A (as depicted in the diagram using the smiley face). Similarly, after receiving user input information covering time window 210B (i.e., user input information covering time periods 200B-D), the emotion detection component 150 may determine the emotional state of the user after time window 210B based on analyzing that user input information. In this example, the emotion detection component 150 determines that the user is in a neutral emotional state after time window 210B (as depicted in the diagram using a neutral face). In a similar manner, as shown in the diagram, the emotion detection component 150 may determine that user remains in a neutral emotional state after time window 210C and after time window 210D, but then is in an angry emotional state after time window 210E and after time window 210F (as depicted in the diagram using an angry face). Thus, in this example, the emotional pattern of the user is one that goes from happy to neutral to sad.

Figure 3:
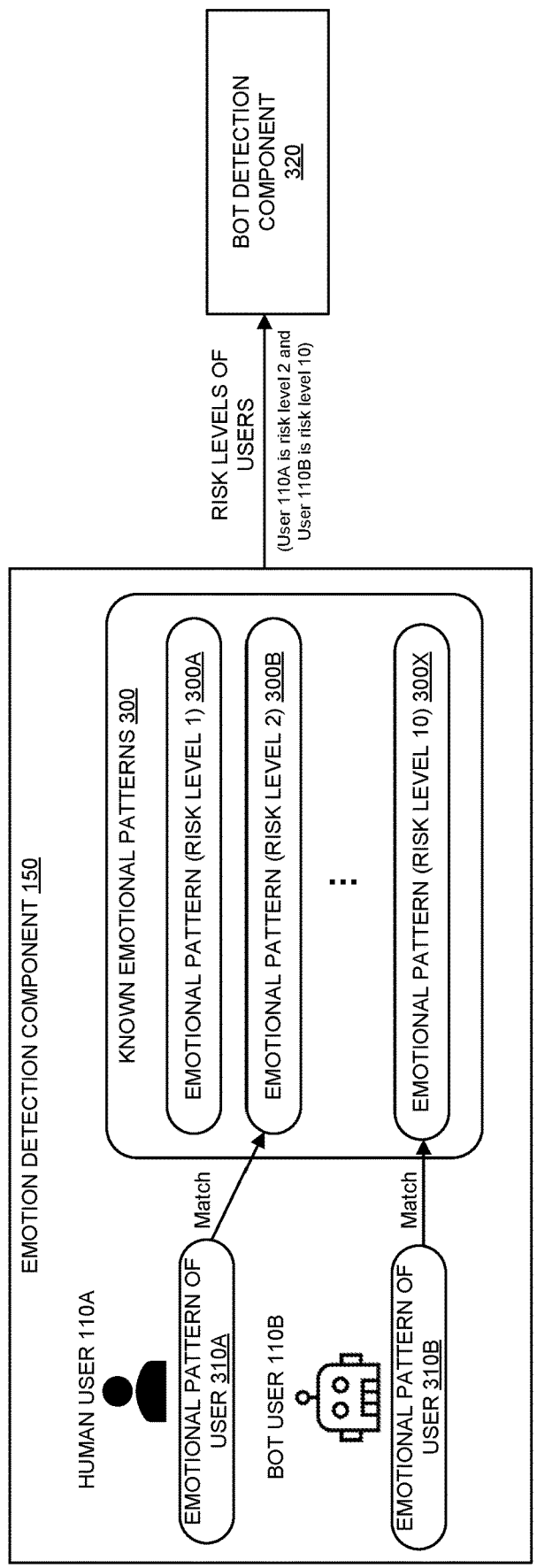
FIG. 3 is a block diagram illustrating emotional pattern matching, according to some embodiments.

FIG. 3 is a block diagram illustrating emotional pattern matching, according to some embodiments. As shown in the diagram, the emotion detection component 150 may include a set of known emotional patterns 300A-X. Each of the known emotional patterns may be associated with a security risk level. In the example shown in the diagram, the security risk level is indicated on a scale from 1 to 10, where 1 is the lowest risk and 10 is the highest risk. For example, as shown in the diagram, emotional pattern 300A is associated with security risk level 1 (e.g., because it has been found that emotional pattern 300A is typically associated with a human user), emotional pattern 300B is associated with security risk level 2, and emotional pattern 300X is associated with security risk level 10 (e.g., because it has been found that emotional pattern 300X is typically associated with a bot user).

The emotion detection component 150 may determine an emotional pattern of a user based on analyzing user input information, as described above. In this example, the emotion detection component 150 determines that user 110A, which in this example is a human user, has emotional pattern 310A. Similarly, the emotion detection component 150 determines that user 110B, which in this example is a bot user, has emotional pattern 310B.

The emotion detection component 150 may then determine whether the emotional pattern of a user 110 matches any of the known emotional patterns and if so assign, to the user 110, the security risk level associated with the matching emotional pattern. For example, as shown in the diagram, the emotion detection component 150 determines that emotional pattern 310A (the emotional pattern of user 110A) matches known emotional pattern 300B, which is associated with a security risk level of 2. Thus, the emotion detection component 150 may assign a security risk level of 2 to user 110A. Also, as shown in the diagram, the emotional detection component 150 determines that emotional pattern 310B (the emotional pattern of user 110B) matches known emotional pattern 300X, which is associated with a security risk level of 10. Thus, the emotion detection component 150 may assign a security risk level of 10 to user 110B.

The emotion detection component 150 may send the security risk levels assigned to the users to a bot detection component 320 so that the bot detection component 320 can use this information (possibly along with other information) to determine whether which of the users are bot users and which are human users.

Figure 4:
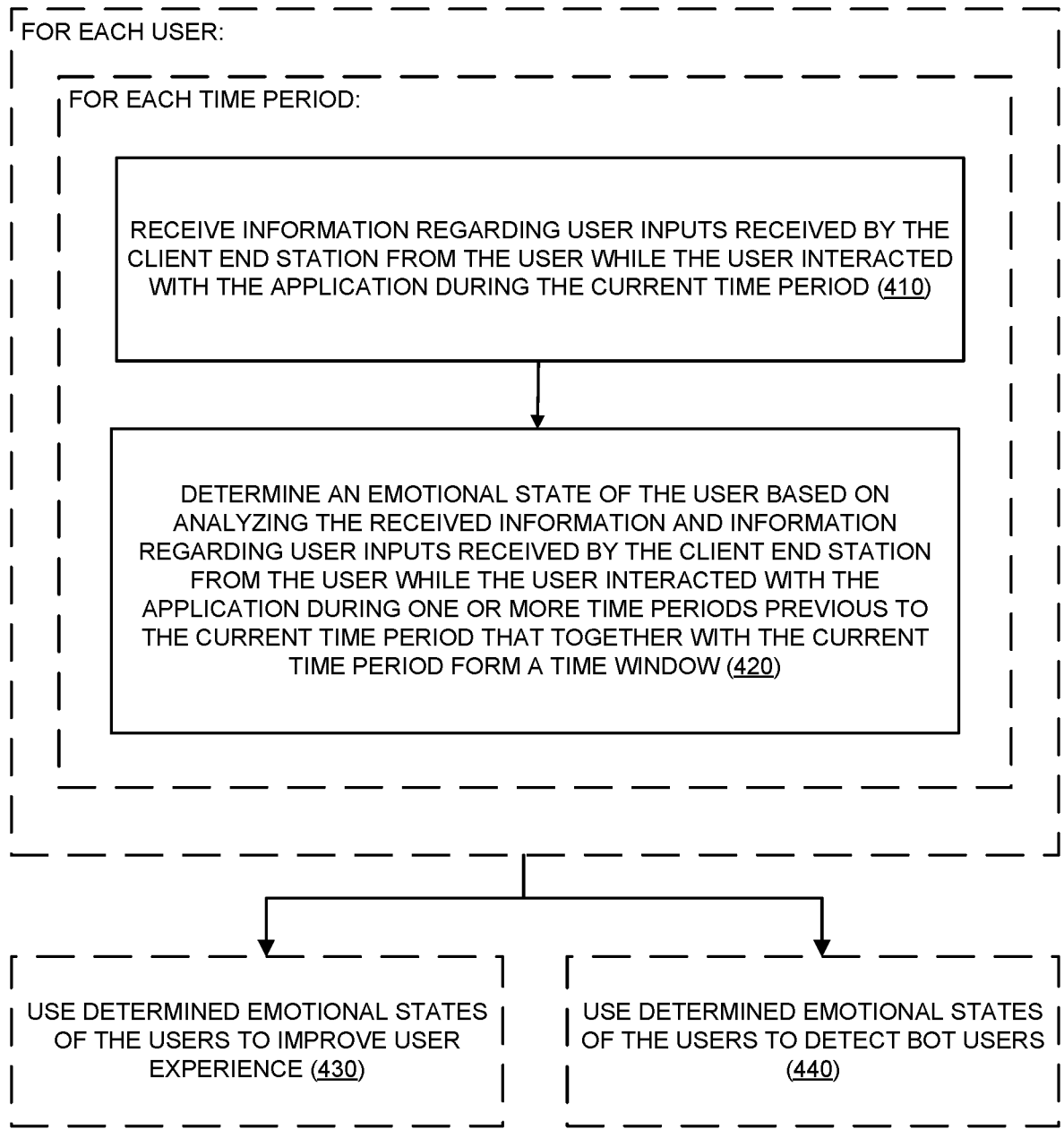
FIG. 4 is a flow diagram of a process for dynamically determining emotional states of users, according to some embodiments.

FIG. 4 is a flow diagram of a process for dynamically detecting emotional states of users, according to some embodiments. In one embodiment, the process is implemented by a network device (e.g., a server end station 130 implementing an emotion detection component 150). Each of the users may operate a client end station to interact with an application. The process may be implemented using hardware, software, firmware, or any combination thereof.

Blocks 410 and 420 may be repeated for each user and for each time period. At block 410, the network device receives information regarding user inputs received by the client end station from the user while the user during the time period. In one embodiment, the information includes statistical information generated by the client end station regarding the user inputs received by the client end station from the user while the user interacted with the application during the time period. In one embodiment, the statistical information generated by the client end station includes statistical information regarding keyboard inputs received by the client end station from the user while the user interacted with the application during the time period, where the statistical information regarding keyboard inputs received by the client end station from the user while the user interacted with the application during the time period includes statistical information regarding key down to key up time length, statistical information regarding key up to key down time length, and/or statistical information regarding a number of keys pressed. Alternatively or additionally, in one embodiment, the statistical information generated by the client end station includes statistical information regarding mouse inputs received by the client end station from the user while the user interacted with the application during the time period, where the statistical information regarding mouse inputs received by the client end station from the user while the user interacted with the application during the time period includes statistical information regarding x-axis movement speed, statistical information regarding y-axis movement speed, statistical information regarding a number of clicks, statistical information regarding click to unclick time length, statistical information regarding unclick to click time length, statistical information regarding x-axis direction changes, statistical information regarding y-axis direction changes, and/or statistical information regarding time lengths between close clicks. Alternatively or additionally, in one embodiment, the statistical information generated by the client end station includes statistical information regarding touchscreen inputs received by the client end station from the user while the user interacted with the application during the time period, where the statistical information regarding touchscreen inputs received by the client end station from the user while the user interacted with the application during the time period includes statistical information regarding x-axis swipe speed, statistical information regarding y-axis swipe speed, statistical information regarding a number of touches, statistical information regarding finger down to finger up time length, statistical information regarding finger up to finger down time length, statistical information regarding touch intensity, statistical information regarding x-axis direction changes, and statistical information regarding y-axis direction changes, and/or statistical information regarding time lengths between close taps.

At block 420, the network device determines an emotional state of the user based on analyzing the received information (the information received at block 410) and information regarding user inputs received by the client end station from the user while the user interacted with the application during one or more time periods previous to the current time period that together with the current time period form a time window. In one embodiment, the emotional state of the user is determined based on a previously determined emotional state of the user (e.g., the immediately previous emotional state of the user).

In one embodiment, at block 430, the determined emotional states of the users are used to improve user experience. As an example, in one embodiment, the network device determines a user interface element of the application that the user was interacting with during a time period and sends an indication to a developer of the application that the user interface element of the application is associated with the emotional state of the user during that time period. As another example, in one embodiment, the network device determines an emotional state of a first user while the first user interacted with the application via a first user interface of the application and determines an emotional state of a second user while the second user interacted with the application via a second user interface of the application (e.g., as part of A/B testing). The network device may then send an indication to a developer of the application that the first user interface of the application is associated with the determined emotional state of the first user and the second user interface of the application is associated with the determined emotional state of the second user.

In one embodiment, at block 440, the determined emotional states of the users are used to detect bot users. For example, in one embodiment, the network device determines an emotional pattern of the user (e.g., based on how the emotional state of the user changes over time) and generates a fingerprint of the user based on the emotional pattern of the user. The fingerprint of the user may be used as part of bot detection to help distinguish between different users/devices. As another example, in one embodiment, the network device determines an emotional pattern of the user and determines whether the emotional pattern of the user matches any known emotional patterns, where each of the known emotional pattern is associated with a security risk level. If the network device determines that the emotional pattern of the user matches one of the known emotional patterns then the network device may assign the security risk level associated with the matching one of the known emotional patterns to the user. In one embodiment, the known emotional patterns include an emotional pattern that has been determined to be associated with a bot user.

Figure 5:
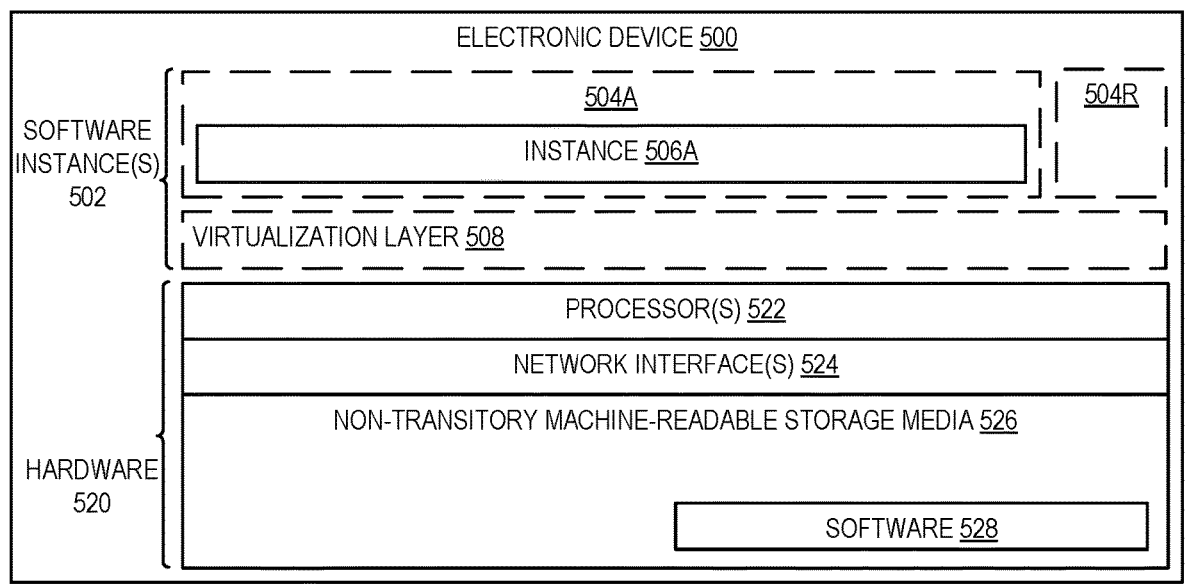
FIG. 5 is a block diagram illustrating an electronic device, according to some embodiments.

FIG. 5 is a block diagram illustrating an electronic device, according to some embodiments. FIG. 5 illustrates hardware 520 comprising a set of one or more processor(s) 522, a set of one or more network interfaces 524 (wireless and/or wired), and non-transitory machine-readable storage medium/media 526 having stored therein software 528 (which includes instructions executable by the set of one or more processor(s) 522). Software 528 can include code, which when executed by hardware 520, causes the electronic device 500 to perform operations of one or more embodiments described herein (e.g., operations for dynamically detecting emotional states of users).

In electronic devices that use compute virtualization, the set of one or more processor(s) 522 typically execute software to instantiate a virtualization layer 508 and software container(s) 504A-R (e.g., with operating system-level virtualization, the virtualization layer 508 represents the kernel of an operating system (or a shim executing on a base operating system) that allows for the creation of multiple software containers 504A-R (representing separate user space instances and also called virtualization engines, virtual private servers, or jails) that may each be used to execute a set of one or more applications; with full virtualization, the virtualization layer 508 represents a hypervisor (sometimes referred to as a virtual machine monitor (VMM)) or a hypervisor executing on top of a host operating system, and the software containers 504A-R each represent a tightly isolated form of a software container called a virtual machine that is run by the hypervisor and may include a guest operating system; with para-virtualization, an operating system or application running with a virtual machine may be aware of the presence of virtualization for optimization purposes). Again, in electronic devices where compute virtualization is used, during operation an instance of the software 528 (illustrated as instance 506A) is executed within the software container 504A on the virtualization layer 508. In electronic devices where compute virtualization is not used, the instance 505A on top of a host operating system is executed on the "bare metal" electronic device 500. The instantiation of the instance 506A, as well as the virtualization layer 508 and software containers 504A-R if implemented, are collectively referred to as software instance(s) 502.

Alternative implementations of an electronic device may have numerous variations from that described above. For example, customized hardware and/or accelerators might also be used in an electronic device.

The techniques shown in the figures can be implemented using code and data stored and executed on one or more electronic devices (e.g., an end station, a network device). Such electronic devices, which are also referred to as computing devices, store and communicate (internally and/or with other electronic devices over a network) code and data using computer-readable media, such as non-transitory machine-readable storage media (e.g., magnetic disks, optical disks, random access memory (RAM), read-only memory (ROM); flash memory, phase-change memory) and transitory computer-readable communication media (e.g., electrical, optical, acoustical or other form of propagated signals, such as carrier waves, infrared signals, digital signals). In addition, electronic devices include hardware, such as a set of one or more processors coupled to one or more other components, e.g., one or more non-transitory machine-readable storage media to store code and/or data, and a set of one or more wired or wireless network interfaces allowing the electronic device to transmit data to and receive data from other computing devices, typically across one or more networks (e.g., Local Area Networks (LANs), the Internet). The coupling of the set of processors and other components is typically through one or more interconnects within the electronic device, (e.g., busses, bridges). Thus, the non-transitory machine-readable storage media of a given electronic device typically stores code (i.e., instructions) for execution on the set of one or more processors of that electronic device. Of course, various parts of the various embodiments presented herein can be implemented using different combinations of software, firmware, and/or hardware. As used herein, a network device (e.g., a router, switch, bridge) is an electronic device that is a piece of networking equipment, including hardware and software, which communicatively interconnects other equipment on the network (e.g., other network devices, end stations). Some network devices are "multiple services network devices" that provide support for multiple networking functions (e.g., routing, bridging, switching), and/or provide support for multiple application services (e.g., data, voice, and video).

The operations in the flow diagrams have been described with reference to the exemplary embodiments of the other diagrams. However, it should be understood that the operations of the flow diagrams can be performed by embodiments of the invention other than those discussed with reference to these other diagrams, and the embodiments of the invention discussed with reference these other diagrams can perform operations different than those discussed with reference to the flow diagrams.

Similarly, while the flow diagrams in the figures show a particular order of operations performed by certain embodiments, it should be understood that such order is exemplary (e.g., alternative embodiments may perform the operations in a different order, combine certain operations, overlap certain operations, etc.).

While the invention has been described in terms of several embodiments, those skilled in the art will recognize that the invention is not limited to the embodiments described, can be practiced with modification and alteration within the spirit and scope of the appended claims. The description is thus to be regarded as illustrative instead of limiting.

What is claimed is:

1. A method by a network device for dynamically detecting emotional states of a user operating a client end station to interact with an application hosted by a server end station, the method comprising:
receiving first information regarding user inputs received by the client end station from the user while the user interacted with the application during a first time period;
determining a first emotional state of the user based on analyzing the first information and information regarding user inputs received by the client end station from the user while the user interacted with the application during one or more time periods previous to the first time period that together with the first time period form a first time window;

receiving second information regarding user inputs received by the client end station from the user while the user interacted with the application during a second time period; and determining a second emotional state of the user based on analyzing the second information and information regarding user inputs received by the client end station from the user while the user interacted with the application during one or more time periods previous to the second time period including at least the first time period that together with the second time period form a second time window.

2. The method of claim 1, wherein the second information includes statistical information generated by the client end station regarding the user inputs received by the client end station from the user while the user interacted with the application during the second time period.

3. The method of claim 2, wherein the statistical information generated by the client end station includes statistical information regarding keyboard inputs received by the client end station from the user while the user interacted with the application during the second time period, wherein the statistical information regarding keyboard inputs received by the client end station from the user while the user interacted with the application during the second time period includes one or more of: statistical information regarding key down to key up time length, statistical information regarding key up to key down time length, and statistical information regarding a number of keys pressed.

4. The method of claim 2, wherein the statistical information generated by the client end station includes statistical information regarding mouse inputs received by the client end station from the user while the user interacted with the application during the second time period, wherein the statistical information regarding mouse inputs received by the client end station from the user while the user interacted with the application during the second time period includes one or more of: statistical information regarding x-axis movement speed, statistical information regarding y-axis movement speed, statistical information regarding a number of clicks, statistical information regarding click to unclick time length, statistical information regarding unclick to click time length, statistical information regarding x-axis direction changes, statistical information regarding y-axis direction changes, and statistical information regarding time lengths between close clicks.

5. The method of claim 2, wherein the statistical information generated by the client end station includes statistical information regarding touchscreen inputs received by the client end station from the user while the user interacted with the application during the second time period, wherein the statistical information regarding touchscreen inputs received by the client end station from the user while the user interacted with the application during the second time period includes one or more of: statistical information regarding x-axis swipe speed, statistical information regarding y-axis swipe speed, statistical information regarding a number of touches, statistical information regarding finger down to finger up time length, statistical information regarding finger up to finger down time length, statistical information regarding touch intensity, statistical information regarding x-axis direction changes, and statistical information regarding y-axis direction changes, and statistical information regarding time lengths between close taps.

6. The method of claim 1, wherein the second emotional state of the user is determined based on the first emotional state of the user.

7. The method of claim 1, further comprising:
determining an emotional pattern of the user based on the first emotional state and the second emotional state.

8. The method of claim 7, further comprising:
generating a fingerprint of the user based on the emotional pattern of the user.

9. The method of claim 7, further comprising:
determining whether the emotional pattern of the user matches any known emotional patterns, wherein each of the known emotional pattern is associated with a security risk level; and
responsive to a determination that the emotional pattern of the user matches one of the known emotional patterns, assigning the security risk level associated with the matching one of the known emotional patterns to the user.

10. The method of claim 9, wherein the known emotional patterns include an emotional pattern that has been determined to be associated with a bot user.

11. The method of claim 1, further comprising:
determining a user interface element of the application that the user was interacting with during the second time period; and
sending an indication to a developer of the application that the user interface element of the application is associated with the second emotional state of the user.

12. The method of claim 1, further comprising:
receiving third information regarding user inputs received by a second client end station from a second user while the second user interacted with the application during a third time period; and
determining an emotional state of the second user based on analyzing the third information.

13. The method of claim 12, wherein the user inputs received by the client end station from the user while the user interacted with the application during the second time period are user inputs received by the client end station while the user interacted with the application via a first user interface of the application, wherein the user inputs received by the second client end station from the second user while the user interacted with the application during the third time period are user inputs received by the client end station while the second user interacted with the application via a second user interface of the application, wherein the method further comprises:
sending an indication to a developer of the application that the first user interface of the application is associated with the second emotional state of the user and the second user interface of the application is associated with the emotional state of the second user.

14. A set of one or more non-transitory machine-readable storage media storing instructions which, when executed by one or more processors of one or more network devices, causes the one or more network devices to perform operations for detecting emotional states of a user operating a client end station to interact with an application hosted by a server end station, the operations comprising:
receiving first information regarding user inputs received by the client end station from the user while the user interacted with the application during a first time period;

determining a first emotional state of the user based on analyzing the first information and information regarding user inputs received by the client end station from the user while the user interacted with the application during one or more time periods previous to the first time period that together with the first time period form a first time window;

receiving second information regarding user inputs received by the client end station from the user while the user interacted with the application during a second time period; and determining a second emotional state of the user based on analyzing the second information and information regarding user inputs received by the client end station from the user while the user interacted with the application during one or more time periods previous to the second time period including at least the first time period that together with the second time period form a second time window.

15. The set of one or more non-transitory machine-readable storage media of claim 14, wherein the second information includes statistical information generated by the client end station regarding the user inputs received by the client end station from the user while the user interacted with the application during the second time period.

16. The set of one or more non-transitory machine-readable storage media of claim 15, wherein the statistical information generated by the client end station includes statistical information regarding keyboard inputs received by the client end station from the user while the user interacted with the application during the second time period.

17. The set of one or more non-transitory machine-readable storage media of claim 15, wherein the statistical information generated by the client end station includes statistical information regarding mouse inputs received by the client end station from the user while the user interacted with the application during the second time period.

18. A network device configured to detect emotional states of a user operating a client end station to interact with an application hosted by a server end station, the network device comprising:

one or more processors; and a non-transitory machine-readable storage medium having instructions stored therein, which when executed by the one or more processors, causes the network device to:

receive first information regarding user inputs received by the client end station from the user while the user interacted with the application during a first time period;

determine a first emotional state of the user based on analyzing the first information and information regarding user inputs received by the client end station from the user while the user interacted with the application during one or more time periods previous to the first time period that together with the first time period form a first time window;

receive second information regarding user inputs received by the client end station from the user while the user interacted with the application during a second time period; and determine a second emotional state of the user based on analyzing the second information and information regarding user inputs received by the client end station from the user while the user interacted with the application during one or more time periods previous to the second time period including at least the first time period that together with the second time period form a second time window.

19. The network device of claim 18, wherein the instructions when executed by the one or more processors, further causes the network device to:

determine an emotional pattern of the user based on the first emotional state and the second emotional state.

20. The network device of claim 19, wherein the instructions which when executed by the one or more processors, further causes the network device to:

determine whether the emotional pattern of the user matches any known emotional patterns, wherein each of the known emotional pattern is associated with a security risk level; and responsive to a determination that the emotional pattern of the user matches one of the known emotional patterns, assign the security risk level associated with the matching one of the known emotional patterns to the user.

* * * * *